(12) United States Patent
Behr et al.

(10) Patent No.: US 6,423,702 B1
(45) Date of Patent: Jul. 23, 2002

(54) PROCESS FOR THE HYDROXYLATION OF AN ACYCLIC OR CYCLIC METHYLENE RADICAL IN THE ALLYLIC POSITION, PHARMACEUTICAL COMPOSITION CONTAINING HYDROXYCHOLESTEROL DERIVATIVES AND UTILIZATION OF SUCH COMPOSITIONS FOR THE PREPARATION OF DRUGS

(75) Inventors: Patrick Behr, Sarreguemine; Alexandre Kupferberg; Marcel Mersel, both of Strasbourg; Alain Privat, St. Clement-la-Riviere Cedex, all of (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 907 days.

(21) Appl. No.: 09/063,784

(22) Filed: Apr. 22, 1998

Related U.S. Application Data (62) Division of application No. 08/598,058, filed on Feb. 7, 1996, which is a continuation of application No. 08/459,406, filed on Jun. 2, 1995, now abandoned, which is a continuation of application No. 08/030,301

(60) Provisional application No. PCT/FR91/00608, filed on Jul. 24, 1991, now abandoned.

(30) Foreign Application Priority Data

Jul. 25, 1991 (FR) .......................................... 90 09501

(51) Int. Cl.$^7$ .............................................. A61K 31/56
(52) U.S. Cl. ........................ 514/182; 424/450; 552/542
(58) Field of Search .......................... 424/450; 514/182; 552/542

(56) References Cited

U.S. PATENT DOCUMENTS

| 4,246,347 A | 1/1981 | Neidleman et al. .......... 435/105 |
| 4,247,641 A | 1/1981 | Neidleman et al. .......... 435/123 |
| 4,284,723 A | 8/1981 | Neidleman et al. .......... 435/123 |

FOREIGN PATENT DOCUMENTS

GB        1 603 864        12/1981

OTHER PUBLICATIONS

Chemical Abstracts, vol. 99, No. 21, 169724u, p. 87, Nov. 21, 1983.
Chemical Abstracts, vol. 85, No. 3, 16176c, p. 259, Jul. 19, 1976.
Chemical Abstracts, vol. 98, No. 21, 177739x, p. 523, May 23, 1983.
Chemical Abstracts, vol. 111, No. 25, 224898x, p. 23, Dec. 18, 1989.
Kupferberg et al, Biochem Biophys. Acta, 1013(3), pp. 231–238 (1989).

*Primary Examiner*—Sreeni Padmanabhan
(74) *Attorney, Agent, or Firm*—Jacobsoh Holman, PLLC (57) ABSTRACT

A pharmaceutical composition conatining at least one C3-OH ether or fatty acid monoester of 7B-hydroxycholesterol selected from the group consisting of the ethers or esters of palmitic, oleic, hexenoic, decenoic and arachindonic acids or esters. The composition is useful as a cytotoxic agent for the treatment on cells having a high proliferative potential.

18 Claims, 8 Drawing Sheets

FIG_7A

FIG. 7B

FIG_8A

FIG_8B

PROCESS FOR THE HYDROXYLATION OF AN ACYCLIC OR CYCLIC METHYLENE RADICAL IN THE ALLYLIC POSITION, PHARMACEUTICAL COMPOSITION CONTAINING HYDROXYCHOLESTEROL DERIVATIVES AND UTILIZATION OF SUCH COMPOSITIONS FOR THE PREPARATION OF DRUGS

This is a divisional application of application Ser. No. 08/598,058, filed Feb. 7, 1996, which is a continuation of application Ser. No. 08/459,406, filed Jun. 2, 1995 (abandoned), which is a continuation of application Ser. No. 08/030,301, filed Mar. 25, 1993 (abandoned), which is a 371 of PCT/FR91/00608, filed Jul. 24, 1991.

The present invention relates to a process for the enzymatic hydroxylation of an acyclic or cyclic methylene in the allylic position, without affecting the other functional groups present on the molecule.

In particular the present invention relates to a process for synthesizing steroid-type compounds hydroxylated in a position a to a double bond.

It also relates to the use of molecules thus synthesized as cyclotoxic agents active against cells which have a high proliferative potential.

The steroids are molecules which comprise a cyclopentanophenanthrene skeleton, widely distributed in the living world, and which have great physiological significance. This structure is thus found in bile acids, sex or cortical hormones, certain vitamins, and cardenolides of plant origin.

A great number of them have a therapeutic potential or properties, and it is thus particularly useful to have available a simple and inexpensive process for synthesizing them. A key stage of this synthesis consists of the selective hydroxylation of certain positions of the skeleton.

Among the steroids which are of significance, the cardenolides constitute a group of steroids having 23 carbons which exist in the form of glucosides in various plants, mainly in the foxglove, lily and corn crowfoot families. Many of these glucosides have a considerable cardiotonic activity and some are used in therapeutics, especially digitalin, digitoxin and digoxin. Schematically, the aglucon part of these molecules is characterized by the presence of a "butenolide"-type (unsaturated lactone) side chain, a 14-hydroxyl in the cis position with respect to the 18 methyl and a 3-hydoxyl [sic]. For example, this structure is found in the digitoxigenin molecule of formula:

The sugars which form a glucoside with the steroid via a bond established with the C-3 hydroxyl comprise glucose and rhamnose, as well a certain number of unusual sugars, such as 2,6-dideoxyhexose, often methylated in the C-3 position.

The way to construct an α,β, lactone [sic] on C17 [lacuna] cyclic structure necessary for the pharmacological activity of this type of compound has been described, especially by Marini-Bettolo et al., (Can. J. Chem. 1981, 59, 1403–1404). Conventionally, 17-keto-α,β-ene derivatives are used as starting compound and lithium ethoxyacetalide [sic], lithium β-furyl and lithium 2-methoxyfuryl are used as reactants. These processes of synthesis cannot be used on the industrial scale because they have a certain number of disadvantages. The time required to obtain the product is relatively long and, moreover, the synthesis is carried out under severe conditions (organic solvents, high temperature). Moreover, the yield of the reaction is low (of the order of 10%) and the purification of the product is difficult, in view of the many additional products which appear during the reaction. Finally, the starting material is both very expensive and very difficult to obtain.

Another group of steroid compounds which has a potential significance in therapeutics consists of the oxysterols, the structure of which derives directly from that of cholesterol via the presence of one or more oxygenated functional groups carried either by the rings or by the side chain of cholesterol. A role in the inhibition of cholesterol synthesis was first attributed to the oxysterols.

The oxysterols were then studied as antiproliferative agents.

In a recent review, Smith & Johnson (Free Radical Biology and Medicine, 1989, 7, 285–332) itemize the mammary cells attacked in vitro by these compounds. In a completely different approach, Cheng et al., (J. Chem. Res., 1977, 217, 2501–2521) have isolated and identified antitumoral active principles from drugs used in the traditional Chinese pharmacopoeia.

Thus the drug Bombix Cum Botryte [sic] contains 7β-hydroxycholesterol which has a cytotoxic activity against cultured cells showing significant multiplication, such as lymphoma (mouse RDM4 and YAC-1) (Cancer Biochem. Biophys., 1986, 9, 75–83), HTC cells (rat liver tumoral cells) (Biochem. Biophys. Res. Commun., 1984, 120, 192–198), rat fibroblasts originating from the heart (C.R. Acad. Sci. Paris, 1984, 299, 221–225) and rat liver epithelial cells (Cell Biol. Toxicol., 1989, 5, 261–270). On the other hand, cells which have a weaker potential for division and which achieve a certain degree of differentiation when cultured, such as cultured heart cells and hepatocytes from newborn rats, are not detrimentally affected by this molecule. The cytotoxicity of 7-hydroxycholesterol [sic] is shown by a halt in cell growth, followed by morphological modifications which precede the detachment and the rapid lysis of the cells.

Rong et al., (C.R. Acad. Sci. Paris, 1985, 300, 89–94) have shown that the sodium salts of 7β-hydroxycholesterol 3,7-bis(hemisuccinate) have an antitumoral activity, injected intraperitoneally into mice carrying ascitic tumors, [lacuna] Krebs-II transplantable carcinoma. It [sic] also shown, in female Sprague-Dawley rats, that (22 R)-cholest-5-ene-3β, 7β22-triol effectively reduced the development of tumors induced by 7,12-di-methylbenz(α)anthracene [sic] (Iversen et al., Virchows Archiv B, 1986, 51, 313–320).

It is generally assumed that the cytotoxic effect of the oxysterols results from the superimposition of several phenomena, the most important of which are the inhibition of the synthesis of cholesterol by inhibition of a key enzyme (HMGR) and a destabilization of the plasmic membranes. In this context, and with a long-term therapeutic prospective, the inventors have studied the effects and the mechanism of action of 7β-hydroxycholesterol on spontaneously transformed lines obtained from primary cultures of astrocytes from newborn rats (normal cells). In the central nervous system (CNS), the astrocytes (glial cells) have retained the potentiality of multiplying, which phenomenon is manifested in certain pathological states, such as reactional gliosis (inflammation) and formation of glioblastomas (neoplasia).

Now, a recent publication shows that 7β-hydroxycholesterol is metabolized, in transformed astrocytes, to esters of fatty acids.

The conventional route of chemical synthesis used for obtaining 7β-hydroxycholesteryl ester resorts to 7-ketocholesterol as starting material.

(70% B)

After esterification of the OH in the 3-position, the functional group is reduced with NaBH$_4$. The two a and β, isomers are obtained with a yield of 70% for the β isomer. This process is difficult to transpose to the industrial level, given its duration.

This is why the present invention relates to a gentle process for the hydroxylation of an acyclic or cyclic methylene radical in the allylic position, characterized in that a peroxidase, iodide ions and hydrogen peroxide (H$_2$O$_2$) are reacted with this methylene radical to produce a compound hydroxylated in a position a to a double bond.

The peroxidase used is preferably lactoperoxidase (LPO), the iodide ions generally arise from KI and the hydrogen peroxide can be generated in situ.

In contrast to the conventional processes for hydroxylation, this process does not involve a powerful reducing agent.

The OH radical is provided by the decomposition of H$_2$O$_2$, catalyzed by lactoperoxidase, an enzyme which is commercially available at reasonable cost.

The reaction can be carried out at temperatures of between 20° C. and 40° C., and will not affect functional groups present on the molecule.

The present invention thus relates to a process for the hydroxylation of an acyclic or cyclic methylene in the allylic position, characterized in that the starting compound contains at least one unprotected ester functional group, and in that this ester functional group is recovered intact in the compound after hydroxylation.

The present invention also relates to a process for the hydroxylation of an acyclic or cyclic methylene in the allylic position, in which the starting compound contains an ether functional group.

The allylic methylene radical is preferably:

a secondary carbon (1) arranged on [sic] the following Scheme Ia:

Ia in which the carbon (2) is preferably connected to a hydrogen or to other carbons.

As an example of a compound of this type, there may be mentioned derivatives:

hydroxylation being carried out on the terminal carbon of the double bond with migration of the latter. This type of compound being able [sic] to contain other substituents, with the proviso that there are no other allylic methylenic carbons.

or else a secondary carbon (1) arranged according to the following Scheme Ib:

in which (A) is a cyclic structure which is preferably of pregnane type; for example, the methylenic carbon which is in the 7-position of the Δ5-pregnene [sic] cyclic system.

By way of example, there may be mentioned:

the hydroxylation being carried out at a position α to the (6–7) double bond. This type of compound being able [sic] to contain other substituents with the proviso that there are no other allylic-methylenic [sic] carbons.

It is thus that the present invention relates to a process for hydroxylation, characterized in that LPO, KI and H₂O₂ are reacted with Δ22-23-norcholene [sic] 3-acetate of formula:

and in that Δ17-20-norcholene-23-ol [sic] 3-acetate of formula:

is obtained in a single stage.

Δ22-23-Norcholene [sic] 3-acetate is obtained from cholanic acid-3-ol. This compound, whose purchasing price is not very high, is easily converted to Δ22-23-norcholene-3-ol [sic] according to the modified process of Vaida et al., (Tetrahedon Lett., 1968, 50, 5173–5174).

Δ17-20-Norcholene-23-ol [sic] 3-acetate then makes it possible, by a series of reactions schematicized below, to obtain a cardenolide aglucon.

This process is simple, requires little energy, its duration is short and its cost price low, in view of the low cost of the reactants. Additionally, the reaction has a good yield and makes it possible to prepare the product on the semi-macro scale, with few additional products.

Indeed, as a result of its specificity, the use of an enzyme as catalyst promotes the production of a major product.

This synthetic route makes it possible to activate the 17,20 and 23 carbons. For this reason, other conversions can be carried out before the final product is obtained. By this process, products having a greater pharmacological activity and lower toxicity can be obtained.

According to another aspect of the invention, the process for hydroxylation is characterized in that a peroxidase, iodide ions and hydrogen peroxide are reacted with a C3 monoester of cholesterol of formula:

in which R represents a carbon chain corresponding to a fatty acid, and in that an ester of 7-hydroxycholesterol of formula:

is obtained in the form of a mixture of esters of 7α- and 7β-hydroxycholesterol.

The fatty acids are universal constituents of all the lipid compounds and are in majority containing even numbers of carbon atoms (at least 4) and containing a linear chain. The natural fatty acids can be saturated or unsaturated and generally they then have from 2 to 6 double bonds; there also exist natural fatty acids having triple bonds.

These fatty acids can esterify the alcohol functional group in the 3-position of the cholesterol molecule. In contrast to the monoesters of 7-keto-cholesterol used for the preparation of the hydroxyl derivatives, the monoesters of cholesterol are readily available at a cost which is not very high.

The reaction is performed in a single stage, at a temperature between 20° C. and 37° C., in a lipophilic organic solvent.

A mixture of α and β isomers of 7-hydroxycholesteryl esters is obtained with proportions of 50% and 50% respectively. The yield can be optimized by adaptation of the solvents, concentration of the reactants and the reaction temperature depending on the type of isomer desired.

The present invention also relates to substituted or unsubstituted fatty acid esters at the C$_3$ [sic] position of β-hydroxycholesterol [sic] which can especially be obtained by the process according to the invention. The fatty acids preferably contain from 6 to 24 carbon atoms and can contain one or more unsaturations.

In a preferred aspect of the invention, the starting material is chosen from the group of cholesterol esters comprising cholesterol palmitate, oleate, hexenoate, decenoate and arachidonate.

Palmitic acid is a saturated aliphatic fatty acid of general formula $C_{16}H_{32}O_2$.

Oleic, hexenoic and decenoic acids are monoethenic fatty acids having respectively, for empirical formula, $C_{18}H_{34}O_2$, $C_5H_{10}O_2$ and $C_{10}H_{18}O_2$. Arachidonic acid has four double bonds and corresponds to the formula $C_{20}H_{32}O_2$.

For cytotoxic and antitumoral applications, in the process for the hydroxylation according to the invention of a C3 monoester of cholesterol, the 7β isomer of the hydroxycholesteryl ester obtained is isolated from the reaction mixture, the said isomer belonging to the group comprising especially the esters of palmitic, oleic, hexenoic, decenoic and arachidonic acid.

According to another of its aspects, the process for hydroxylation consists in reacting a peroxidase, iodide ions and hydrogen peroxide with a C3 ether of in which R represents a carbon chain corresponding to a fatty acid, to obtain an ether of 7-hydroxycholesterol of formula:

Preferably, the 7β isomer of the hydroxycholesteryl ether obtained is isolated from the reaction mixture, the said isomer belonging in particular to the group comprising the ethers of palmitic, oleic, hexenoic, decenoic and arachidonic acid.

These compounds can also be synthesized from 7-ketocholesterol and the alkenyl chloride corresponding to the fatty acid, for example CH3—(CH$_2$)$_7$—CH═CH—(CH$_2$)$_7$—CH$_2$Cl for oleic acid. A reduction by NaH$_4$ is then carried out.

The formation of an ether between the carbon chain of the fatty acid and the steroid molecule, in place of an ester functional group, gives a more stable molecule which can resist hydrolysis, especially by hepatic enzymes, and can thus be injected peripherally.

This is why the subject of the present invention is a pharmaceutical composition, characterized in that it contains at least one C3-OH ether of 7β-hydroxycholesterol chosen from the group comprising the ethers of palmitic, oleic, hexenoic, decenoic and arachidonic acid, and a vehicle acceptable for its administration.

Such a composition is useful as a cytotoxic agent on cells which have a high proliferative potential.

The present invention also relates to a pharmaceutical composition, characterized in that it contains at least one C3 fatty acid monoester of 7β-hydroxycholesterol preferably chosen from the group comprising the palmitate, oleate, hexenoate, decenoate and arachidonate, and a vehicle acceptable for its administration.

In particular, the present invention relates to the use of a C$_3$ [sic] monoester of 7β-hydroxycholesterol and of a fatty acid, such as defined above, for the preparation of a pharmaceutical composition intended for the treatment of cells having a high proliferative potential. Indeed, this composition is useful as a cytotoxic agent.

According to another aspect of the invention, a C7 ester of the 7β-hydroxylcholesteryl [sic] ester described above is used. In the case where more hydrophilic compounds are desired, a particularly advantageous molecule is represented by cholesteryl 7-phosphoenolpyruvate 3-oleate.

The liposoluble compounds of 7β-hydroxycholesterol can be put into the form of liposomes or of a combination with phospholipids, such as those used in the preparation of the liposomes, and especially phosphatidylcholine. They can also be used in combination, in the liposomes, with GM1- and GT1b-type gangliosides. This combination between gangliosides and C3 esters of 7β-hydroxycholesterol makes it possible to obtain a vector which is smaller in size and more hydrophilic.

These liposomes will be administered parenterally with an acceptable vehicle.

These compositions have a great affinity for nervous tissue which is rich in lipids.

The compositions containing an ether or an ester of β-hydroxycholesterol and of fatty acid, incorporated in liposomes containing phosphatidylcholine and, for example, monosialoganglioside (GM1), are thus particularly useful as antitumoral [lacuna] on intracerebral glioblastoma-type tumors of the nervous system, or as an agent for the treatment of reactional glioses.

The present invention thus relates to the preparation of a pharmaceutical composition containing at least one C3 monoester of 7β-hydroxycholesterol in the form of liposomes, and useful as an antitumoral agent. According to one aspect of the invention, this pharmaceutical composition is characterized in that it is useful on tumors of the nervous system, in particular glioblastomas. The injection of liposomes containing phosphatidylcholine and certain esters of 7β-hydroxycholesterol causes significant regression of the subcutaneous glioblastomas induced in rats.

According to another aspect of the invention, the pharmaceutical composition containing a monoester of 7β-hydroxycholesterol in the form of liposomes is used as an anti-inflammatory agent of the nervous system, in particular in reactional glioses.

The examples which follow are intended to illustrate the invention without in any way limiting its scope.

BRIEF DESCRIPTION OF THE DRAWINGS

Reference will be made to the following appended figures.

EXAMPLE 1

MATERIALS AND REAGENTS

Thin silica layers (TLC) with or without fluorescence indicator F254 (Merck, FRG)

HPLC column: silica column (5μ, 3.9 mm×15 cm) (Waters, USA)

HPLC equipment (Waters Associated, USA)

Gas phase chromatography (SE30-type capillary column) coupled to the mass spectrometry (LKB 9000, Sweden)

200 or 400 MHz NMR (Bruker, FRG)

Electronic microscopy (Philips EM300, Netherlands)

Ultrasonic disintegrator (Sonimasse S20 or Soniprep 150, France)

Contrasting phase or light microscopy (Nikon, Japan)

UV lamp (Bioblock, France)

Lactoperoxidase (EC 1.11.1.7, 60 IU/mg of proteins, Sigma, USA)

$H_2O_2$, (Prolabo RP, Normapur, France)

Rabbit anti-GFAP (Glial Fibrillary Acid Protein) antibodies (Dakopatts Denmark)

Secondary antibodies coupled to the peroxidase (Biosys, France)

The cell clones (glioblastomas) were provided by Prof. Benda (Science, 1968, 161, 370–371).

The other reagents and solvents are of Analar type.

HPLC

The products extracted from the TLCs were eluted at 500 p.s.i. in n-heptane/isopropanol (99/1 v/v) (flow rate of 1.5 ml/min) and detected by a spectrophotometer at 220 nm. After evaporation and dilution in the appropriate solvent or/and silylation (Kupferberg et al., Biochim. Biophys. Acta., 1989, 1013, 231–238). [sic]. The harvested samples are subjected to analysis by NMR and/or by mass spectrometry coupled to gas phase chromatography (GC-MS)

GC-MS:

GC : Column: 25 m, internal diameter 0.32 mm (SE30) Carrier gas : 15 p.s.i. helium Temperature program : 100° C. to 300° C. (3° C./min) ROS-type injector (280° C.)

MS : Separation temperature : 250° C. Source temperature : 250° C. Electronic energy : 70 eV Acceleration potential : 3500 V

NMR:

The compounds to be analyzed were dissolved in $CDCl_3$.

EXAMPLE 2

SYNTHESIS OF Δ17-20-NORCHOLENE-3.23-DIOL [sic] (Icl)

4 mg of Δ22-23-norcholene-3-ol [sic] are withdrawn from a chloroform solution ($CHCl_3$) and the solvent evaporated in a round-bottomed flask under a nitrogen atmosphere, 0.9 ml of dimethyl sulfoxide is added to the residue and the entire contents are heated at $_{30}$° C. for a few minutes. There are added to this solution, in order:

15 ml of phosphate buffer (50 mM, pH 6.0, Pi)

1 ml of Pi containing 15 mg of KI

450 μl of Pi containing 450 μg of LPO.

The reaction is initiated by adding 300 μl of 1.3% $H_2O_2$ every 15 sec and this 10 times in succession. Mixing of the reaction mixture is carried out with a magnetic bar. The reaction mixture is then extracted successively with 20 ml, 5 ml and 5 ml of $CHCl_3$. The combined chloroform phases are separated with 10 ml [lacuna] $H_2O_2$. The organic phase is then filtered on anhydrous sodium sulfate and evaporated. Chromatography of the products is carried out by TLC with three successive elutions in the system of solvents (cyclohexane/etyl [sic] acetate, 2/1 v/v) and the products are detected either at 254 nm or with the reagent of Macala et al., (J. Lipid Res., 1983, 24, 1243–1250). The products are extracted from the silica with $CHCl_3$-methanol (1:1 v/v), evaporated and subjected to analysis.

RESULTS:

The NMR spectrum shows the appearance of two peaks at 0.67 and 0.73 ppm, which are attributed to the resonance of the 18-methyl of two geometric isomeric products. Our reasons are the following:

the 21-methyl appears as two"singlets" in place of the "doublet" observed for the starting material (Δ22-23-norcholene-3-ol [sic]);

vinylic protons are not detected;

two additional protons are detected in the neighborhood of the 3-proton. Their complex shape and distribution suggest long-range effects on the chemical shift of these two protons.

The appearance of two protons in a low magnetic field and the complexity of their spectrum show the presence of a (Δ17-20) [sic] double bond.

The probable structure of the compound is thus 3,23-dihydroxy-Δ17-20-norcholene [sic] in the form of two geometric isomers. The NMR of the acetylated Icl product confirms our analysis.

The yield of this enzymatic synthesis is 90%.

EXAMPLE 3

SYNTHESIS OF Δ22-23-NORCHOLENE [sic] 3-ACETATE 4 mg of Δ22-23-norcholene-3-ol [sic] are dissolved in 2 ml of $CHCl_3$ and 100 μl of anhydrous pyridine and 300 μl of anhydrous acetic [lacuna] are added. The reaction mixture is continually mixed at room temperature for 24 h. After evaporation under nitrogen, the products are fractionated and detected as described in the above example.

EXAMPLE 4

SYNTHESIS OF Δ17-20-NORCHOLENE-23-ol [sic] 3-ACETATE

The preparation of the reagents and the synthesis are carried out at 30° C. 4 mg of Δ22-23-norcholene [sic] 3-acetate are withdrawn from a chloroform solution and the $CHCl_3$ evaporated in a round-bottomed flask under a nitrogen atmosphere; 1 ml of dimethyl sulfoxide is added to the residue and there are then added, in order:

11 ml of Pi (dropwise)

500 μl of Pi containing 7.5 mg of KI 1.7 ml of a solution composed of 1 ml of 1.3% $H_2O_2$ and of 0.7 ml containing 200 μg of LPO.

At the end of 1 h, a few crystals of sublimed $I_2$ (approximately 2 mg) are added and, at the end of 6 hours, there are added:

500 μl of Pi containing 7.5 mg of KI 1 ml of 1.3% $H_2O_2$ 0.2 ml of Pi containing 200 4g [sic] of LPO.

This last operation is repeated after 24 h. The extraction, fractionation and detection of the products are carried out according to Example 2.

RESULTS:

Silylation of Ic and the GC-MS show the mass of the supposed compound less a fragment with a mass of 42 (M-42); the mass 42 corresponds to a fragment of the acetyl, cleaved during electron impact. This result shows the presence of the acetyl and hydroxyl groups.

The NMR, which shows the arrangement of the "doublet" (21-methyl) resonating at 1.02 and 1.03 ppm and the "quadruplet" and "quintuplet" resonating at 4.83 and 5.82 ppm respectively (protons 23 and 22), argues in favor of the migration of the 22-23 double bond between the (Δ17-20) [sic] tertiary carbons. The appearance of a "triplet" at 3.12 ppm, of another centered at 3.65 ppm and split into a double doublet, and of a "doublet" centered at 3.90 ppm argues in favor of the ($—CH_2[C22]-CH_2OH[C23]$) group close to the (Δ17-20) [sic] double bond.

The yield of this enzymatic synthesis is 70%.

EXAMPLE 5

SYNTHESIS OF 7β-CHOLESTERYL PALMITATE (C16:0)

40 μg of cholesteryl palmitate are withdrawn from a chloroform solution and the $CHCl_3$ evaporated under nitrogen; 100 μl of dimethyl sulfoxide and 200 μl of ether [($CH_3CH_2)O$] [sic] are added to the residue and the solution heated successively at 100° C. for 20 min and at 120° C .for 15 min in a hermetic chamber. The solution is equilibrated at 37° C. and the reaction is carried out at this temperature. 670 μl of Pi are added (dropwise) as well as 200 μl of Pi containing 200 μl of LPO, 50 μl of Pi containing 750 μg of KI and 10 μl of Pi containing 1.3% $H_2O_2$ every 15 sec and this 10 times. After incubating for 30 min, the cycle (LPO, KI, $H_2O_2$) is repeated a second time and, at the end of 1 h, the products are extracted with 4 ml of $CHCL_3$, the chloroform phases are combined and rinsed twice with 4 ml of $H_2O$. After evaporation, the products are fractionated by TLC with three successive elutions in the hexane/ether (8/2 v/v) solvent system. The products are then detected and extracted from the silica as described in Example 2.

EXAMPLE 6

SYNTHESIS OF 7β-CHOLESTERYL OLEATE (MET C18:1)

40 μg of cholesteryl oleate are withdrawn from a chloroform solution and the $CHCl_3$ evaporated under nitrogen; 100 μl of dimethyl sulfoxide and 100 μl of benzene are added and the mixture is subjected to ultrasound for 30 sec at an amplitude of 180 μat room temperature. 200 μl of Pi containing 200 μg of LPO and 50 μl of Pi containing 75 μg of KI are rapidly added. The reaction is initiated with the addition of 10 μl of PI containing 1.3% $H_2O_2$ ten times every 15 sec. The $LPO/KI/H_2O_2$ cycle is repeated after 30 min and, at the end of 1 h, the products are extracted, chromatographed and identified as described in Examples 5 and 2 respectively.

RESULTS OF ENZYMATIC SYNTHESIS OF 7β—OH—CH [sic] PALMITATE OR OLEATE

The C3-OH esters (C16:0 and C18:1) of 7β-OH-CH were synthesized chemically according to Scheme II and were used as standards for the identification of these same, enzymatically synthesized (LPO), molecules by GC-MS, in view of the microquantities of material used.

GC-MS analysis clearly shows that 7β-OH-cholesteryl palmitate and oleate have been obtained respectively. The yield of the reaction is 10% and that of the α and β isomers, 50% and 50% respectively.

EXAMPLE 7

IN VIVO REACTIONAL GLIOSES AND TREATMENT

Preparation of the liposomes (phosphatidvlcholine (PC)/ steroids)

PC and steroidal derivatives are dissolved in $CHCL_3$/ methanol [sic] (2/1 v/v), the solvent evaporated and 1 ml of KCL [sic] (0.15 M) added. The suspension is subjected to ultrasound in an ice bath (5×1 min with an interval of 30 sec, amplitude 18 μm), centrifuged 13,000 g for 20 min, the supernatant withdrawn and concentrated 5 times under nitrogen. BRAIN Rats aged 6 days are anesthetized with an intraperitoneal injection of imalgene 500 (2 mg/10 g) and valium (0.05 ml/10 g) and then placed in a stereotaxic apparatus in order to be subjected to an electrolytic lesion at the level of the striatum. For this, a dental probe, insulated except at the point, is moved down to the level of the striatum according to the stereotaxic coordinates with respect to the lambda. At this level, a current of 2 mA is applied for 10 secs;

2 μl of a suspension of liposomes containing 20 μg of PC and 2 μg of various sterols or oxysterols are injected into the site of lesion.

SPINAL CORD

After complete section of the spinal cord at the T8 level in rats weighing 250 g (Sprague, Dawley, EFFA, Credo), 5 μl of a suspension of liposomes containing 500 μg of PC and 50 μg of esters of 7β-OH-CH (C18:0 or C18:1) are injected at 0.5 mm downstream of the section.

DETECTION OF THE REACTIVE ASTROCYTES

GFAP, specific structural labeler of astrocytes, is detected on paraffin sections by the antibody/antiantibody system to GFAP coupled to the peroxidase. The addition of 4-chloronaphthol and $H_2O_2$ shows the presence of GFAP.

EFFECT OF THE ESTERS OF 7β-OH-CH ON IN VIVO C3-OH SUBCUTANEOUS GLIOBLASTOMAS AND REACTIONAL GLIOSES

Figure 1:
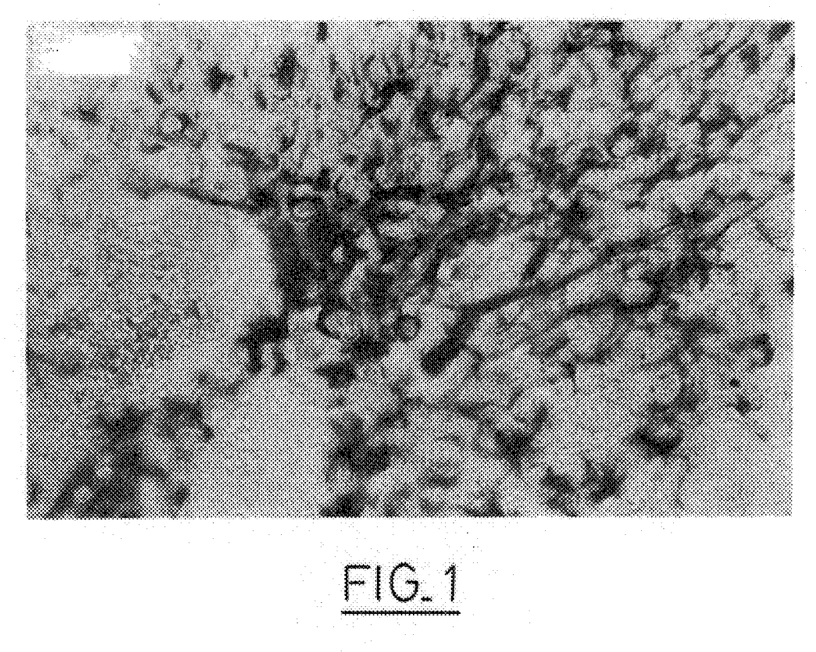
FIG. 1: Reactional gliosis; treatment with cholesteryl oleate.
Figure 2:
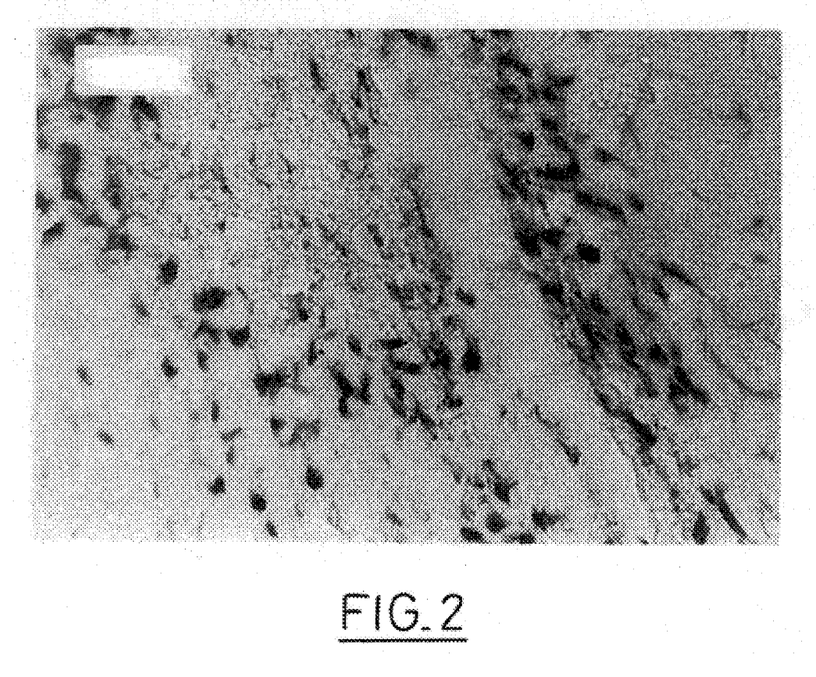
FIG. 2: Reactional gliosis; treatment with 7β-OH-CH (7β-hydroxycholesterol).
Figure 3:
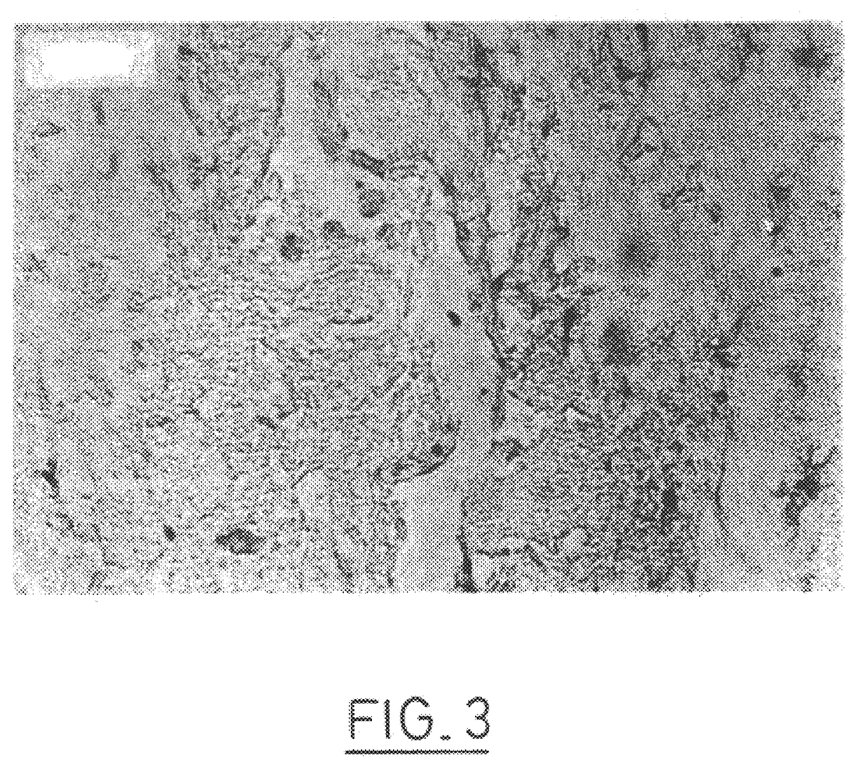
FIG. 3: Reactional gliosis; treatment with 7β-OH-cholesteryl 3-oleate.

The invention of liposomes containing 7β-OH-CH (C18:1) shows a high attenuation of reactional gliosis in the CNS (FIG. 3) with respect to the injection of 7β-OH-CHj (FIG. 2) or CH (C18:1) (FIG. 1). Likewise, the injection of liposomes containing either PC, or PC/CH, or PC/CH (C16:0), and, or PC/7β-OH-CH (C18:0) is shown to be ineffective. The injection of liposomes [lacuna] PC/7β-OH-CH (C18:1) next to the spinal cord lesion site also reduces secondary reactional gliosis.

EXAMPLE 8

INDUCTION OF IN VIVO SUBCUTANEOUS TUMORS AND TREATMENT

The C6 cells (passage 55–57) are injected subcutaneously at the shoulders at a charge of 106 cells/200 μl of 9% NaCl in rats (26 g) aged 3 weeks according to Ledig et al., (Revue de l'Alcoolisme, 1986, 31, 1–11); when the tumors develop (2 weeks after inoculating with the C6 cells), 50 μl of a suspension of liposomes containing 1 mg of PC and 100 μg of cholesteryl oleate or 7β-OH-cholesteryl oleate are injected into the tumors. The animals are photographed 48 hours afterwards.

RESULT ON THE SUBCUTANEOUS GLIOBLASTOMAS

Figure 4:
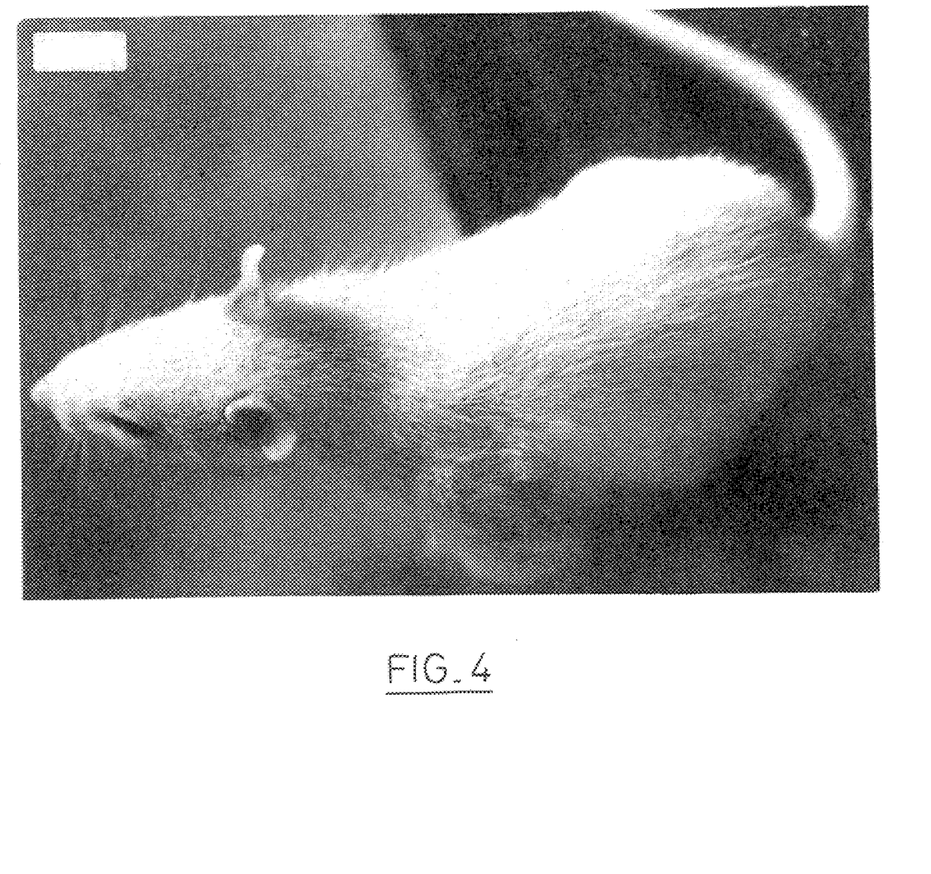
FIG. 4: Subcutaneous tumor induced in rats by inoculating with C6 cells.
Figure 5:
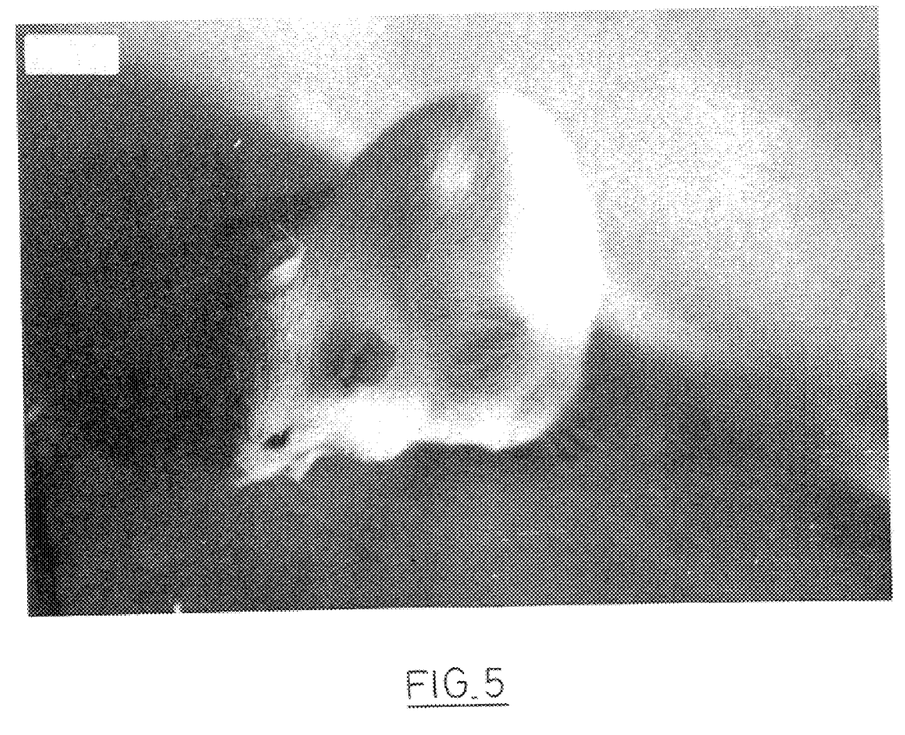
FIG. 5: Treatment of subcutaneous tumors with cholesteryl oleate.
Figure 6:
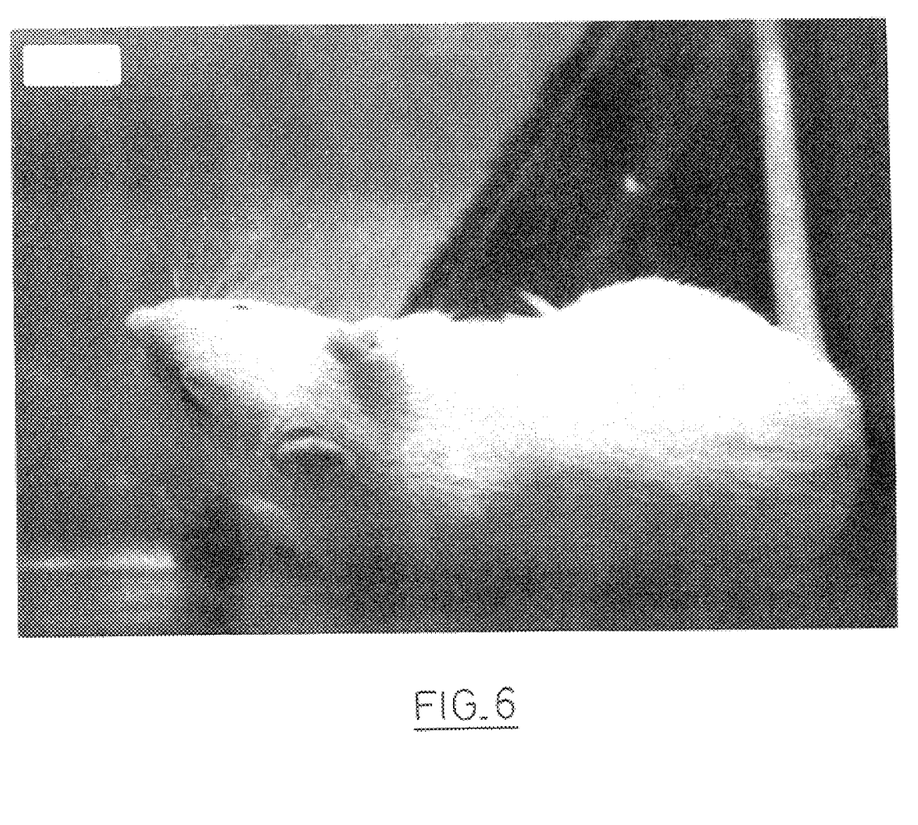
FIG. 6: Treatment of subcutaneous tumors with 7β-OH-cholesteryl 3-oleate.

FIG. 4 shows a tumor which has developed in a male rat by inoculation with C6 cells; while the injection of liposomes containing PC/CH (C18:1) has practically no effect (FIG. 5), that of liposomes containing PC/7β-OH-CH (C18:1) causes significant regression of the tumor (FIG. 6).

EXAMPLE 9

ACTIVITY ON IN VIVO GLIOBLASTOMAS OF THE C18:1 ESTER

INDUCTION OF TUMORS IN THE BRAIN

The "in vivo" model proposed by Galli et al., (J. Neurooncology, 7, 299–304, 1989) has been adopted with a few modifications in the number of C6-type cells injected and in the age of the rats. Rats (Wistar male) aged 6 days are anesthetized and placed in a stereotaxic apparatus, the skin of the cranium is opened and the skull pierced at appropriate coordinates (4.5 AP, 3.0 ML, 2.0 mm DV with respect to the lambda, set 0) using a dental drill; $200 \times 10^3$ C6 in 5 ml of PBS are then injected over 4 minutes and then the skin sutured. 72 hours later, the rats are operated on again and treated with liposomes containing the 7β-hydroxycholesteryl 3-esters.

PREPARATION OF THE LIPOSOMES

The liposomes are prepared according to the method of Manyama et al. Phosphatidylcholine, GM1 (monosialoganglioside) and MET C18:1 (10/1/1 mol/mol/mol) are dissolved in chloroform/methanol (1/1 v/v) and then evaporated under nitrogen. The lipid film is solubilized in 200 μl of PBS containing 4 μM of octyl glucoside. This suspension is then dialyzed against PBS for 6 hours. The BRL-type membranes used have an exclusion limit of 12,000–14,000 KDa and the dialysis is carried out at a pH of 7.4.

TREATMENT OF THE TUMORS

The tumors (4 μl containing 40 μg of MET C18:1) are injected 72 hours after inoculation of the C6 cells in the brain into the site of the tumor using a stereotaxic apparatus.

AUTOPSY AND HISTOCHEMISTRY

The rats are sacrificed 8 days after the treatment by sublethal injection of pentobarbital, perfused with formalin (4%) and the withdrawn brain is post-fixed in formalin (4%) and then in isobutanol and included in paraffin. Sections with a thickness of 10 μm are prepared using a section cutter and, after removing paraffin in toluene, the glioblastomas are detected by staining with Cresyl Violet (0.1% in 0.1 M ethyl acetate and 0.1 M sodium acetate) and subjected to an image analyzer (IBAS, KONTRON, SAMBA ALCATEL).

FIG. 7 shows that the injection of MET C18:1 (40 μg) into the glioblastomas obtained in the rat cortex causes a significant reduction in the size of the tumors.

Figure 7A:
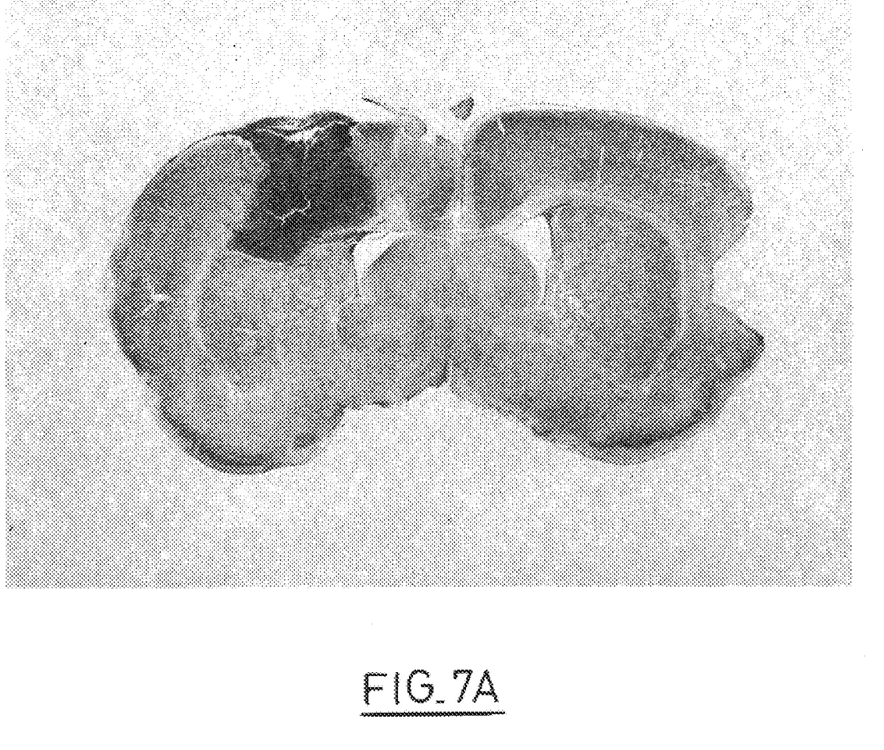
FIG. 7: Optical microscopy of the glioblastomas after staining with Cresyl Violet.

FIG. 7A shows the result obtained after treatment with liposomes containing PC and GM1.

Figure 7B:
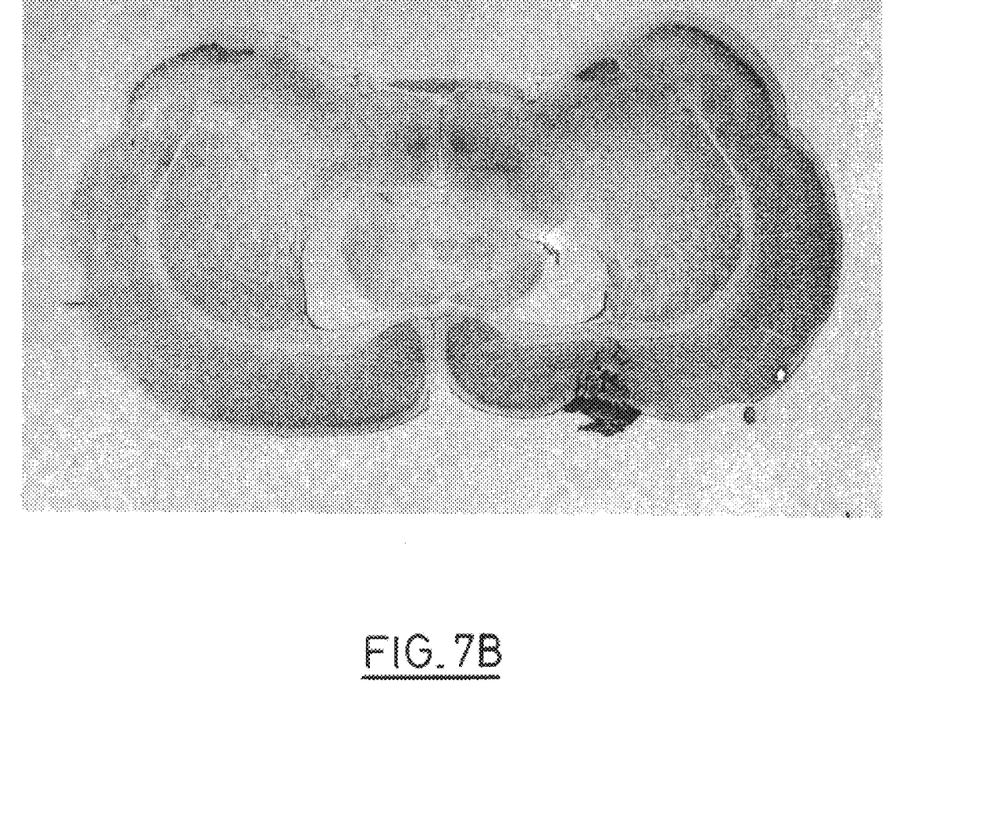
Figure 8A:
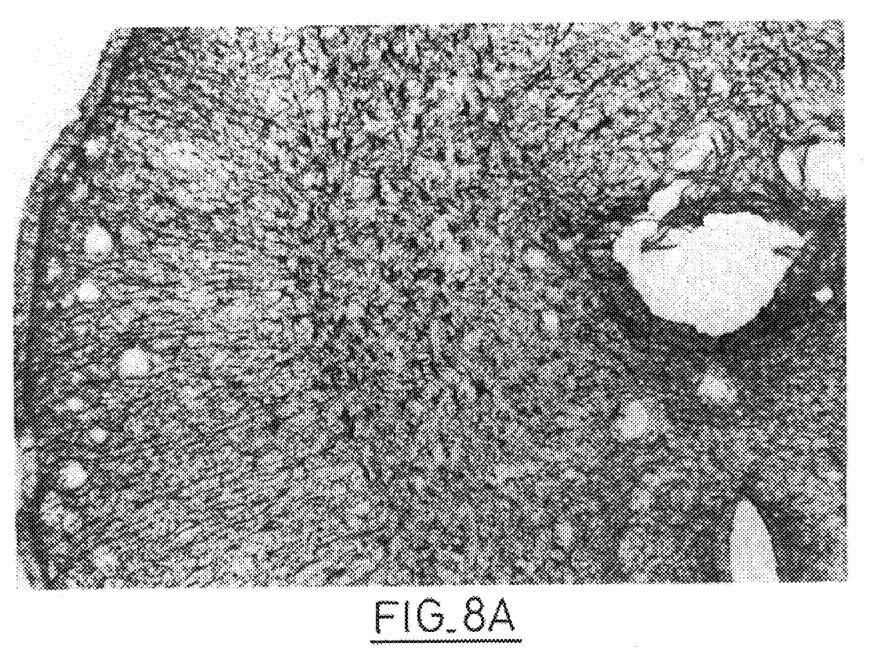
FIG. 8: Immunocytochemical detection of glial fibrillary acid protein (GFAP) in a spinal cord after section. 8A, control rat. 8b, rat treated with liposomes containing 7β-hydroxycholesteryl 3-oleate, phosphatidylcholine and GM1.
Figure 8B:
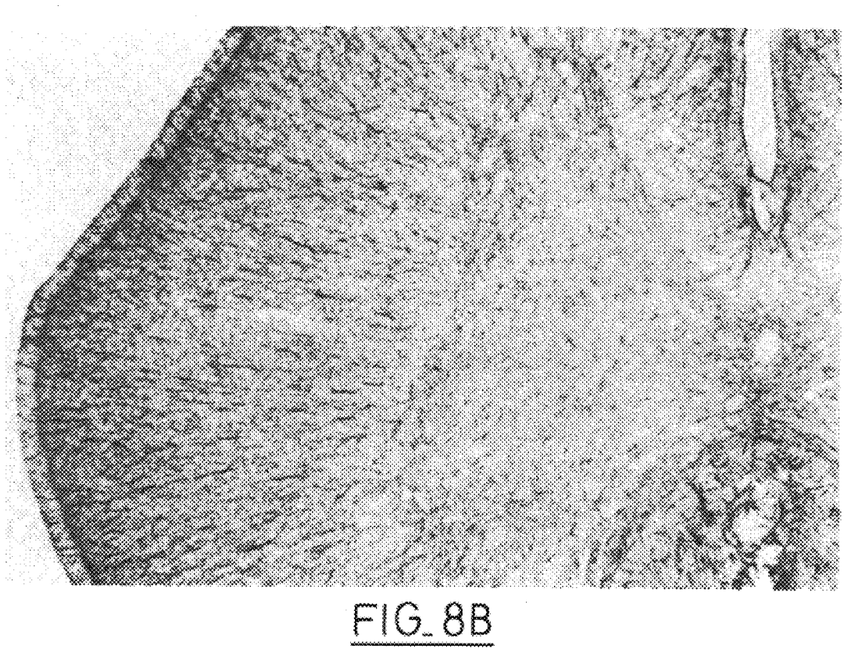

FIG. 7B shows the result obtained after treatment with liposomes containing PC, GM1 and 7β-OH-CH 3-oleate (40 μg).

NUCLEAR MAGNETIC RESONANCE IMAGERY

The images of rat brains are obtained with a Bruker MSL 200 spectrometer equipped with a magnet with a wide opening: 7.8 cm. The magnetic field of 4.7 teslas corresponds to a proton resonance frequency of 200 MHz. The field gradients used make it possible to acquire images having a sectional thickness of 1 mm at mid-height and a field of view of 4 cm, or a side resolution of 0.15 mm for 256×256 images. The sections obtained are frontal.

The animal is anesthetized by intramuscular injection of ketamine (36 mg/kg) and xylazine (5.5 mg/kg). It is fastened onto a support which makes it possible for it to be reproducibly positioned and introduced into an antenna with a useful diameter of 40 mm.

In order to distinguish the various tissues encountered and the lesions (edema, gliosis, tumor) caused and to characterize them by their longitudinal T1 and transverse T2 relaxation times, various acquisition sequences are used.

In a first stage, sequences of rapid imagery are employed for the correct positioning of the sections, localization of the lesions and the determination of the contrast observed (T1, T2). Weighted images in T1 are obtained by the use of the GEFI (gradient echo) sequence with an echo time $T_E$=14 ms, a recovery time $T_r$=175 ms and a switching angle of 30°. Weighted images in T2 are produced with the RARE sequence (strings of echoes with spin differently coded in phase) with $T_z$32 30 ms, and $T_r$32 3000 ms and a RARE factor of 8. These GEFI and RARE images are obtained on several frontal sections in a few minutes (5 to 10 minutes in total). Sixteen joined sections make it possible to study the whole of the brain. For the case of the tumors, Gadolinium [sic] (70 μmol in 9% NaCl) is injected as contrast agent.

Quantitative analysis of the lesions thus observed requires the acquisition of images with sequences of echoes of spin having several echoes and recovery times.

A first series of images is obtained with an MSME (multislices-multiecho) sequence. The acquisition parameters are: $T_E$=30 ms, $T_r$=2646 MS. Six echoes are recorded. In order to improve the signal to noise ratio, two accumulations are carried out. The acquisition time is 23 minutes. The proton density and the transverse relaxation parameter (function of T2 and the diffusion coefficient) are calculated using a model which is monoexponential at each point of the image. Their distributions (mean and standard deviation) are determined in different regions of interest.

Measurement of the longitudinal relaxation parameters requires the acquisition of images with a degree of saturation different from that obtained above. The MSME sequence is then used with a recovery time of 783 ms. Two echoes are recorded. The acquisition time corresponding to two accumulations is 7 minutes. The relaxation time $T_1$ is calculated in each point from the ratio of the acquired images with the two recovery times, according to a development model which takes into account a single relaxation time. The distribution of the $T_1$ is determined on the same regions of interest.

The monitoring over time by NMR imagery of the same glioblastoma induced in the cortex of a rat confirms the regression of the tumor during a treatment with 7β-oh-cholesterol 3-oleate.

What is claimed is:

1. Pharmaceutical composition comprising a therapeutically effective amount of a drug of at least one C3 monoester of 7β-hydroxycholesterol selected from the group consisting of the palmitate, oleate, hexenoate, decenoate and arachidonate, incorporated into a liposome and/or combined with a phospholipid and/or a ganglioside, and a pharmaceutically acceptable vehicle.

2. A method of using a pharmaceutical composition according to claim 1, said pharmaceutical composition having a cytotoxic activity, comprising administering the composition to mammals over a period of time for the treatment of diseases involving cells having a high proliferative potential.

3. The method of claim 2 wherein the composition is injected one or more times into the cells during a stereotaxic procedure.

4. The method of claim 2 wherein the drug is active as an antitumoral agent.

5. The method of claim 2 further comprising administering the drug to mammals for the treatment of tumors of the nervous system.

6. The method of claim 5 wherein the tumor of the nervous system is glioblastomas.

7. The method of claim 5 wherein the tumor is in cystic form.

8. The method of claim 5 wherein the composition is injected one or more times into the tumor during a stereotaxic procedure.

9. The method of claim 2 wherein the drug is administered to mammals for the treatment of reactional glioses.

10. Pharmaceutical composition comprising a therapeutically effective amount of a drug of at least one C3-OH ether of 7β-hydroxycholesterol selected from the group consisting of ethers of palmitic, oleic, hexenoic, decenoic and arachidonic acid, incorporated into a liposome and/or combined with a phospholipid and/or a ganglioside, and a pharmaceutically acceptable vehicle.

11. A method of using a pharmaceutical composition according to claim 10, said pharmaceutical composition having a cytotoxic activity, comprising administering the composition to mammals over a period of time for the treatment of diseases involving cells having a high proliferative potential.

12. The method of claim 11 wherein the composition is injected one or more times into the cells during a stereotaxic procedure.

13. The method of claim 11 wherein the drug is active as an antitumoral agent.

14. The method of claim 11 further comprising administering the drug to mammals for the treatment of tumors of the nervous system.

15. The method of claim 14 wherein the tumor of the nervous system is glioblastomas.

16. The method of claim 14 wherein the tumor is in cystic form.

17. The method of claim 14 wherein the composition is injected one or more times into the tumor during a stereotaxic procedure.

18. The method of claim 11 wherein the drug is administered to mammals for the treatment of reactional glioses.

* * * * *